United States Patent [19]

Benardella

[11] Patent Number: Plant 5,857

[45] Date of Patent: Jan. 20, 1987

[54] ROSE PLANT—BENJEN

[75] Inventor: Frank A. Benardella, Old Tappen, N.J.

[73] Assignee: Nor'East Miniature Roses, Inc., Rowley, Mass.

[21] Appl. No.: 737,735

[22] Filed: May 28, 1985

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Vincent G. Gioia

[57] ABSTRACT

A new miniature rose variety of neyron rose flower coloring but with varying pink tonality and pale yellow petal reverse.

1 Drawing Figure

The present invention relates to a new and distinct variety of rose plant of the miniature rose class, which was originated by my crossing as seed parent the rose known as "Party Girl" and as pollen parent the rose known as "Laguna". The varietal denomination of this new variety is "Benjen".

Among the novel characteristics possessed by this new variety which distinguish it from its parents and all other varieties of which I am aware are its attractive neyron rose colored flowers with varying pink tonality and pale yellow petal reverse that maintain their color and form through development and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Color Chart (R.H.S.C.C.). The terminology used in color description herein refers to plate numbers in the aforementioned color chart, e.g., "55B" in plate 55B of The Royal Horticultural Society Color Chart.

Parentage: Seedling.

*Seed parent.*—"Party Girl".

*Pollen parent.*—"Laguna".

Class: Miniature.

The following observations are made of specimens grown under glass in Essex County, Mass., during the month of March.

FLOWER

Blooming habit: Recurrent.

A. Bud:

(1) *Size.*—Medium.

(2) *Form.*—Long, pointed.

(3) *Color.*—When sepals first divide — petal undersurface visible near 36D, orient pink; petal top surface, near Neyron rose 55B, with near 36A at bud petal edge.

(4) *Sepals.*—Longer than bud, slightly foliated.

(5) *Peduncle.*—Length — about ¾ to 1". Aspect — straight. Strength — erect. Color — near 145B.

B. Bloom:

(1) *Size.*—Averge size when fully expanded — about 1¾ to 2 inches.

(2) *Borne.*—Singly and several together in sprays.

(3) *Form.*—High centered at first, becoming flat, outer petals reflex to point and inner petals roll under upon opening but with pointed apices.

(4) *Petalage.*—Number of petals under normal conditions — 18 to 20.

(5) *Color.*—After sepals fall, petal undersurface coloring, orient pink near 36D, becomes less apparent and petal top surface neyron rose, near 55B and lighter shades 55C and 55D, barely distinguishable from 73B through 73D, appears as predominant flower coloring. Petal edges show lighter toned highlights. Petal top surfaces show veining of tones darker than surrounding area. Petal undersurfaces in partially open to open blooms appear pale yellow with pinkish cast (near 8D blushed with 36C, D) and show veining. Color of petals at point of attachment is near 19D.

C. Petals:

(1) *Texture.*—Thick.

(2) *Appearance.*—Inside — satiny, outside — satiny.

(3) *Form.*—Broad, fan shaped with pronounced apex on many petals.

(4) *Arrangement.*—Regularly arranged, imbricated.

(5) *Petaloids in center.*—Few to none.

(6) *Persistence.*—Drop off cleanly.

(7) *Fragrance.*—Slight.

(8) *Lasting quality.*—Average.

REPRODUCTIVE ORGANS

A. Stamens, filaments and anthers:

(1) *Arrangement.*—Regularly arranged around styles.

(2) *Color.*—Near 26A.

B. Pollen:

*Color.*—Near 25A.

C. Styles: Even length.

D. Stigmas:

*Color.*—Near 32C.

E. Hips: None observed.

PLANT

A. Form: Compact, symmetrical.

B. Growth: Vigorous.

*Height attained.*—About 14 to 16 inches.

C. Foliage: Compound 5 to 7 leaflets.

(1) *Size.*—Medium.

(2) *Quantity.*—Abundant.

(3) *Color.*—New foliage: Upper side — near to 147B with slight near 185A edge. Under side — near to 148B. Old foliage: Upper side — near 139A. Under side — near 147B.

(4) *Shape.*—Oval, pointed.

(5) *Texture.*—Upper side is glossy and under side is matte.

(6) *Edge.*—Serrated.

(7) *Serration.*—Relatively fine.

(8) *Leaf Stem.*—Color — near 148A. Under side — near 146C.

(9) *Stipules.*—Medium smooth.

(10) *Resistance to disease.*—Blackspot — average. Mildew — average. Rust — average.

D. Wood:

(1) *New wood.*—Color — near 148A. Bark — smooth.

(2) *Old wood.*—Color — near 139B. Bark — smooth.

E. Thorns:

(1) *Thorns.*—Quantity (main stalk) — ordinary. On laterals from stalk — average. Form — straight, pointed, angled slightly downward. Length — small. Color — near 185C. Position — irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by neyron rose colored flowers of varying pink tonality and pale yellow petal reverse that hold color well through development and aging.

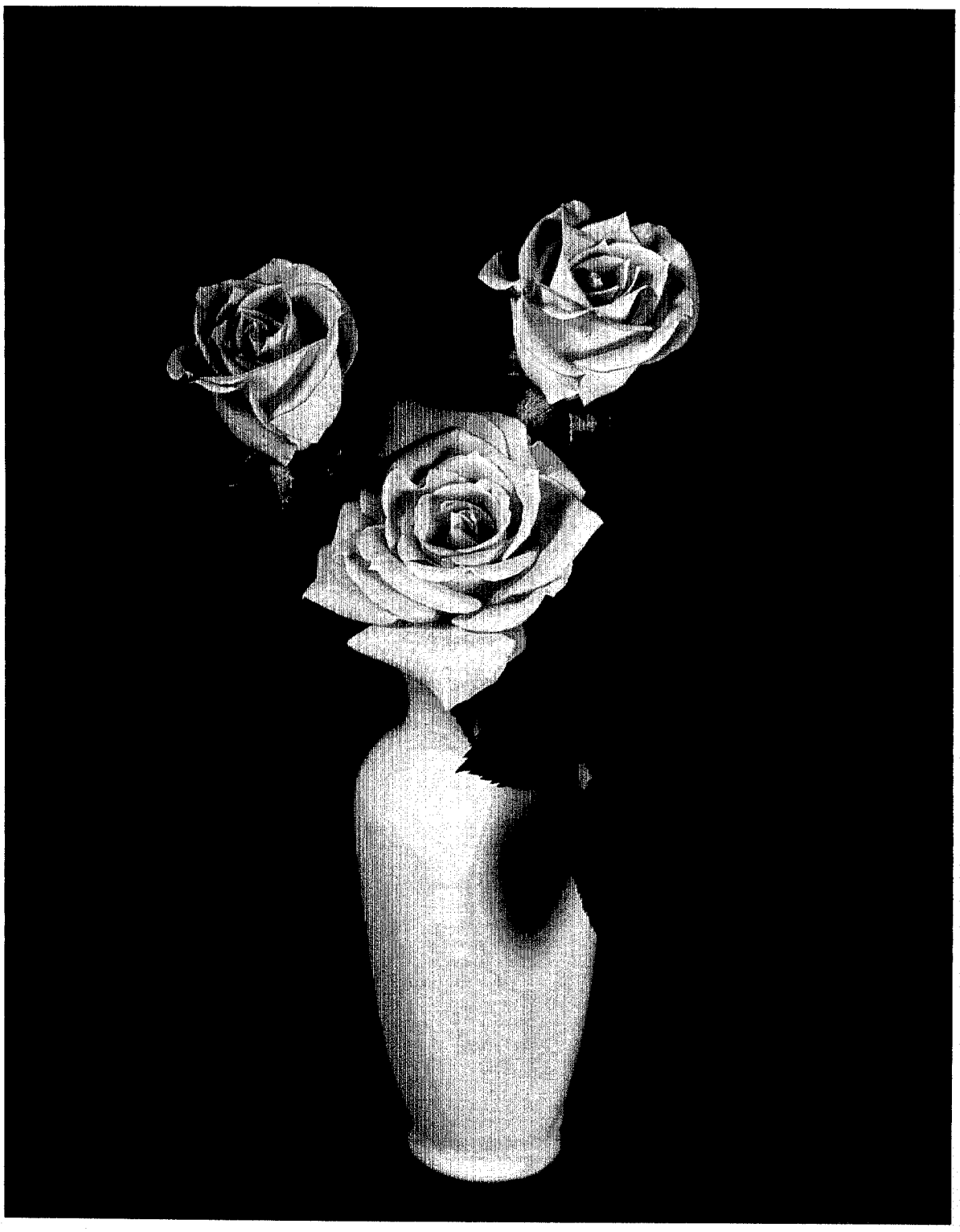

* * * * *